(12) United States Patent
Gunn et al.

(10) Patent No.: US 12,201,385 B2
(45) Date of Patent: *Jan. 21, 2025

(54) USER INTERFACE FOR A SYSTEM USED TO DETERMINE TISSUE OR ARTIFACT CHARACTERISTICS

(71) Applicant: Briteseed, LLC, Chicago, IL (US)

(72) Inventors: Jonathan Gunn, Chicago, IL (US); Hariharan Subramanian, Mundelein, IL (US); Steve McPhilliamy, Chicago, IL (US)

(73) Assignee: Briteseed, LLC, Chicago, IL (US)

( * ) Notice: Subject to any disclaimer, the term of this patent is extended or adjusted under 35 U.S.C. 154(b) by 30 days.

This patent is subject to a terminal disclaimer.

(21) Appl. No.: 17/816,703

(22) Filed: Aug. 1, 2022

(65) Prior Publication Data

US 2022/0361965 A1 Nov. 17, 2022

Related U.S. Application Data

(63) Continuation of application No. 15/698,844, filed on Sep. 8, 2017, now Pat. No. 11,399,898, which is a
(Continued)

(51) Int. Cl.
*A61B 34/00* (2016.01)
*A61B 5/00* (2006.01)
(Continued)

(52) U.S. Cl.
CPC ............ *A61B 34/25* (2016.02); *A61B 5/0084* (2013.01); *A61B 5/489* (2013.01); *A61B 17/282* (2013.01);
(Continued)

(58) Field of Classification Search
CPC ....... A61B 34/25; A61B 34/76; A61B 5/0084; A61B 5/489; A61B 5/02007;
(Continued)

(56) References Cited

U.S. PATENT DOCUMENTS 5,129,400 A 7/1992 Makino et al.
5,259,761 A 11/1993 Schnettler et al.
(Continued)

FOREIGN PATENT DOCUMENTS

EP 2 353 534 8/2011
GB 1 445 678 8/1976
(Continued)

OTHER PUBLICATIONS

Akl et al., Performance Assessment of an Opto-Fluidic Phantom Mimicking Porcine Liver Parenchyma, J. Bio. Optics, vol. 17(7) 077008-1 to 077008-9 (Jul. 2012).
(Continued)

*Primary Examiner* — Katherine M Rodjom
(74) *Attorney, Agent, or Firm* — Cook Alex Ltd.

(57) ABSTRACT

A surgical system includes a shaft having a distal end and a proximal end, the proximal end including a grip, a sensor attached to the distal end of the shaft, at least one visual indicator disposed at the distal end of the shaft, and a controller coupled to the sensor and the at least one visual indicator, the controller actuating the at least one visual indicator according to a signal received from the sensor.

20 Claims, 7 Drawing Sheets

Related U.S. Application Data continuation-in-part of application No. 14/383,173, filed as application No. PCT/US2013/029412 on Mar. 6, 2013, now abandoned.

(60) Provisional application No. 62/384,841, filed on Sep. 8, 2016, provisional application No. 61/607,335, filed on Mar. 6, 2012.

(51) Int. Cl.
    A61B 17/28 (2006.01)
    A61B 90/00 (2016.01)
    A61B 1/313 (2006.01)
    A61B 5/02 (2006.01)
    A61B 17/00 (2006.01)
    A61B 17/29 (2006.01)
    A61B 90/30 (2016.01)

(52) U.S. Cl.
    CPC ............ *A61B 90/36* (2016.02); *A61B 1/3132* (2013.01); *A61B 5/02007* (2013.01); *A61B 2017/00022* (2013.01); *A61B 2017/00057* (2013.01); *A61B 2017/00115* (2013.01); *A61B 2017/00473* (2013.01); *A61B 17/29* (2013.01); *A61B 2017/2926* (2013.01); *A61B 34/76* (2016.02); *A61B 2090/061* (2016.02); *A61B 2090/306* (2016.02); *A61B 2090/309* (2016.02); *A61B 90/361* (2016.02); *A61B 2090/373* (2016.02); *A61B 2090/3929* (2016.02); *A61B 2090/3945* (2016.02); *A61B 2505/05* (2013.01); *A61B 2562/043* (2013.01)

(58) Field of Classification Search
    CPC ..... A61B 17/282; A61B 17/29; A61B 1/3132; A61B 90/361; A61B 2017/00057; A61B 2017/00115; A61B 2017/00473; A61B 2017/2926; A61B 2017/00022; A61B 2562/043
    See application file for complete search history.

(56) References Cited

U.S. PATENT DOCUMENTS

| | | | |
|---|---|---|---|
| 5,762,609 A | 6/1998 | Benaron et al. | |
| 5,769,791 A | 6/1998 | Benaron et al. | |
| 5,772,597 A | 6/1998 | Goldberger et al. | |
| 5,785,658 A | 7/1998 | Benaron et al. | |
| 5,807,261 A | 9/1998 | Benaron et al. | |
| 5,987,346 A | 11/1999 | Benaron et al. | |
| 6,178,340 B1 | 1/2001 | Svetliza | |
| 6,374,128 B1 | 4/2002 | Toida et al. | |
| 6,569,104 B2 | 5/2003 | Ono et al. | |
| 6,594,518 B1 | 7/2003 | Benaron et al. | |
| 6,922,577 B2 | 7/2005 | Nakashima et al. | |
| 7,006,861 B2 | 2/2006 | Flock et al. | |
| 7,112,201 B2 | 9/2006 | Truckai et al. | |
| 7,235,072 B2 | 6/2007 | Sartor et al. | |
| 7,515,265 B2 | 4/2009 | Alfano et al. | |
| 7,740,591 B1 | 6/2010 | Starr et al. | |
| 7,749,217 B2 | 7/2010 | Podhajsky | |
| 7,904,138 B2 | 3/2011 | Goldman et al. | |
| 7,983,738 B2 | 7/2011 | Goldman et al. | |
| 8,058,771 B2 | 11/2011 | Giordano et al. | |
| 8,073,531 B2 | 12/2011 | Goldman et al. | |
| 8,118,206 B2 | 2/2012 | Zand et al. | |
| 8,123,745 B2 | 2/2012 | Beeckler et al. | |
| 8,150,500 B2 | 4/2012 | Goldman et al. | |
| 8,244,333 B2 | 8/2012 | Wood et al. | |
| 8,255,040 B2 | 8/2012 | Goldman et al. | |
| 8,295,904 B2 | 10/2012 | Goldman et al. | |
| 8,380,291 B2 | 2/2013 | Wood et al. | |
| 8,391,960 B2 | 3/2013 | Wood et al. | |
| 8,417,306 B2 | 4/2013 | Cheng | |
| 8,463,364 B2 | 6/2013 | Wood et al. | |
| 8,467,857 B2 | 6/2013 | Kim et al. | |
| 8,478,386 B2 | 7/2013 | Goldman et al. | |
| 8,483,805 B2 | 7/2013 | Takenoshita et al. | |
| 8,483,819 B2 | 7/2013 | Choi et al. | |
| 8,489,178 B2 | 7/2013 | Wood et al. | |
| 8,586,924 B2 | 11/2013 | Demos | |
| 8,649,568 B2 | 2/2014 | Sato | |
| 8,649,848 B2 | 2/2014 | Crane et al. | |
| 8,682,418 B2 | 3/2014 | Tanaka | |
| 8,706,200 B2 | 4/2014 | Goldman et al. | |
| 8,712,498 B2 | 4/2014 | Goldman et al. | |
| 8,750,970 B2 | 6/2014 | Goldman et al. | |
| 8,792,967 B2 | 7/2014 | Sato | |
| 8,818,493 B2 | 8/2014 | Goldman et al. | |
| 8,838,210 B2 | 9/2014 | Wood et al. | |
| 9,526,921 B2 | 12/2016 | Kimball et al. | |
| 2002/0169381 A1 | 11/2002 | Asada et al. | |
| 2003/0036685 A1 | 2/2003 | Goodman | |
| 2003/0036751 A1 | 2/2003 | Anderson et al. | |
| 2003/0120306 A1 | 6/2003 | Burbank et al. | |
| 2004/0111085 A1 | 6/2004 | Singh | |
| 2005/0143662 A1 | 6/2005 | Marchitto et al. | |
| 2005/0180620 A1 | 8/2005 | Takiguchi | |
| 2006/0020212 A1 | 1/2006 | Xu et al. | |
| 2006/0052850 A1 | 3/2006 | Darmos et al. | |
| 2006/0100523 A1 | 5/2006 | Ogle et al. | |
| 2006/0154209 A1* | 7/2006 | Hayman ............... A61C 19/004 433/215 |
| 2006/0155194 A1 | 7/2006 | Marcotte et al. | |
| 2007/0038118 A1 | 2/2007 | DePue et al. | |
| 2007/0142824 A1* | 6/2007 | Devengenzo .......... A61B 34/30 606/1 |
| 2009/0018414 A1 | 1/2009 | Toofan | |
| 2009/0054908 A1 | 2/2009 | Zand et al. | |
| 2009/0062692 A1* | 3/2009 | Ferzli ................... A61B 5/1076 600/587 |
| 2010/0222786 A1 | 9/2010 | Kassab | |
| 2010/0249763 A1 | 9/2010 | Larson et al. | |
| 2011/0021925 A1 | 1/2011 | Wood et al. | |
| 2011/0245685 A1 | 10/2011 | Murata et al. | |
| 2011/0251605 A1 | 10/2011 | Hoarau et al. | |
| 2012/0016362 A1 | 1/2012 | Heinrich et al. | |
| 2012/0046555 A1 | 2/2012 | Takamatsu et al. | |
| 2012/0116267 A1* | 5/2012 | Kimball ................. G16H 20/40 606/1 |
| 2012/0143182 A1 | 6/2012 | Ullrich et al. | |
| 2012/0172842 A1 | 7/2012 | Sela et al. | |
| 2012/0296205 A1* | 11/2012 | Chernov ............ A61B 18/1445 600/431 |
| 2013/0102905 A1 | 4/2013 | Goldman et al. | |
| 2013/0226013 A1 | 8/2013 | McEwen et al. | |
| 2013/0267874 A1* | 10/2013 | Marcotte ............... A61B 5/4893 606/41 |
| 2014/0086459 A1 | 3/2014 | Pan et al. | |
| 2014/0100455 A1 | 4/2014 | Goldman et al. | |
| 2014/0155753 A1 | 6/2014 | McGuire, Jr. et al. | |
| 2014/0194751 A1 | 7/2014 | Goldman et al. | |
| 2014/0236019 A1 | 8/2014 | Rahum | |
| 2014/0276088 A1 | 9/2014 | Drucker | |
| 2014/0313482 A1 | 10/2014 | Shahidi et al. | |
| 2015/0011896 A1 | 1/2015 | Yelin et al. | |
| 2015/0051460 A1 | 2/2015 | Saxena et al. | |
| 2015/0066000 A1 | 3/2015 | An et al. | |
| 2017/0181701 A1 | 6/2017 | Fehrenbacher et al. | |
| 2018/0042522 A1 | 2/2018 | Subramanian et al. | |
| 2018/0098705 A1 | 4/2018 | Chaturvedi et al. | |
| 2018/0289315 A1 | 10/2018 | Chaturvedi et al. | |
| 2019/0038136 A1 | 2/2019 | Gunn et al. | |
| 2019/0046220 A1 | 2/2019 | Chaturvedi et al. | |
| 2019/0175158 A1 | 6/2019 | Chaturvedi et al. | |
| 2020/0268311 A1 | 8/2020 | Shukair et al. | |
| 2020/0337633 A1 | 10/2020 | Chaturvedi et al. | |

(56) References Cited

U.S. PATENT DOCUMENTS

2020/0345297 A1 11/2020 Chaturvedi et al.
2021/0068856 A1 3/2021 Gunn et al.

FOREIGN PATENT DOCUMENTS

| JP | H10-005245 | 1/1998 |
|---|---|---|
| JP | 2003-019116 | 1/2003 |
| JP | 2010-081972 | 4/2010 |
| WO | WO98/27865 | 7/1998 |
| WO | WO2001/060427 | 8/2001 |
| WO | WO2003/039326 | 5/2003 |
| WO | WO2004/030527 | 4/2004 |
| WO | WO2005/091978 | 10/2005 |
| WO | WO2008/082992 | 7/2008 |
| WO | WO2009/144653 | 12/2009 |
| WO | WO2011/013132 | 2/2011 |
| WO | WO2012/158774 | 11/2012 |
| WO | WO2013/134411 | 9/2013 |
| WO | WO2014/194317 | 12/2014 |
| WO | WO2015/148504 | 10/2015 |
| WO | WO2016/134327 | 8/2016 |
| WO | WO2016/134330 | 8/2016 |
| WO | WO2017/062720 | 4/2017 |
| WO | WO2017/139624 | 8/2017 |
| WO | WO2017/139642 | 8/2017 |
| WO | WO2018/044722 | 3/2018 |
| WO | WO2019/050928 | 3/2019 |
| WO | WO2019/126633 | 6/2019 |
| WO | WO2019/143965 | 7/2019 |
| WO | WO2020/041203 | 2/2020 |
| WO | WO2020/142394 | 7/2020 |

OTHER PUBLICATIONS

Comtois et al., A Comparative Evaluation of Adaptive Noise Cancellation Algorithms for Minimizing Motion Artifacts in a Forehead-Mounted Wearable Pulse Oximeter, Conf. Proc. IEEE Eng. Med. Biol. Soc., 1528-31 (2007).
Figueiras et al., Self-Mixing Microprobe for Monitoring Microvascular Perfusion in Rat Brain, Med. Bio. Eng'r Computing 51:103-112 (Oct. 12, 2012).
Hammer et al., A Simple Algorithm for In Vivo Ocular Fundus Oximetry Compensating for Non-Haemoglobin Absorption and Scattering, Phys. Med. Bio. vol. 47, N233-N238 (Aug. 21, 2002).
Ibey et al., Processing of Pulse Oximeter Signals Using Adaptive Filtering and Autocorrelation to Isolate Perfusion and Oxygenation Components, Proc SPIE, vol. 5702, 54-60 (2005).
Li et al., Pulsation-Resolved Deep Tissue Dynamics Measured with Diffusing-Wave Spectroscopy, Optics Express, vol. 14, No. 17, 7841-7851 (Aug. 21, 2006).
Mendelson et al., In-vitro Evaluation of a Dual Oxygen Saturation/Hematocrit Intravascular Fiberoptic Catheter, Biomed Instrum. Technol. 24(3):199-206 (May/Jun. 1990).
Phelps et al., Rapid Ratiometric Determination of Hemoglobin Concentration using UV-VIS Diffuse Reflectance at Isobestic Wavelengths, Optics Express, vol. 18, No. 18, 18779-18792 (Aug. 30, 2010).
Subramanian, Real Time Perfusion and Oxygenation Monitoring in an Implantable Optical Sensor, Thesis Texas A&M Univ. (Dec. 2004).
Subramanian, Real-Time Separation of Perfusion and Oxygenation Signals for an Implantable Sensor Using Adaptive Filtering, IEEE Trans. Bio. Eng'g, vol. 52, No. 12, 2016-2023 (Dec. 2005).
Subramanian, An Autocorrelation-Based Time Domain Analysis Technique for Monitoring Perfusion and Oxygenation in Transplanted Organs, IEEE Trans. Bio. Eng'g, vol. 52, No. 7, 1355-1358 (Jul. 2005).

* cited by examiner

USER INTERFACE FOR A SYSTEM USED TO DETERMINE TISSUE OR ARTIFACT CHARACTERISTICS The present application is a continuation of U.S. application Ser. No. 15/698,844, filed Sep. 8, 2017, which (i) claims the benefit of U.S. Provisional App. No. 62/384,841, filed Sep. 8, 2016, and (ii) is a continuation in part of U.S. application Ser. No. 14/383,173, which is a U.S. National Stage of PCT International Patent Application No. PCT/US2013/029412, filed Mar. 6, 2013, which claims the benefit of U.S. Provisional App. No. 61/607,335, filed Mar. 6, 2012, all of which are hereby incorporated herein by reference.

BACKGROUND

This patent is directed to a user interface for a system used to determine characteristics of tissue or an artifact, such as a vessel, and in particular to a user interface of a system used to determine characteristics of tissue or an artifact, where the system includes at least one light emitter and at least one light sensor disposed at a distal end of a shaft.

Systems and methods that identify artifacts, and in particular vessels, in the surgical field during a surgical procedure provide valuable information to the surgeon or surgical team. U.S. hospitals lose billions of dollars annually in unreimbursable costs because of inadvertent vascular damage during surgery. In addition, the involved patients face a mortality rate of up to 32%, and likely will require corrective procedures and remain in the hospital for an additional nine days, resulting in tens, if not hundreds, of thousands of dollars in added costs of care. Consequently, there is this significant value to be obtained from methods and systems that permit accurate determination of the presence of vessels, such as blood vessels, in the surgical field, such that these costs may be reduced or avoided.

Systems and methods that provide information regarding the presence of blood vessels in the surgical field are particularly important during minimally invasive surgical procedures. Traditionally, surgeons have relied upon tactile sensation during surgical procedures both to identify blood vessels and to avoid inadvertent damage to these vessels. Because of the shift towards minimally invasive procedures, including laparoscopic and robotic surgeries, surgeons have lost the ability to use direct visualization and the sense of touch to make determinations as to the presence of blood vessels in the surgical field. Consequently, surgeons must make the determination whether blood vessels are present in the surgical field based primarily on convention and experience. Unfortunately, anatomical irregularities frequently occur because of congenital anomalies, scarring from prior surgeries, and body habitus (e.g., obesity). Systems and methods that would permit surgeons to determine the presence and/or the characteristics of vessels in the surgical field during surgery (potentially in real time or near real time) under such conditions would be a significant advantage.

On the other hand, while it would be advantageous to include systems and methods that provide information regarding the presence of blood vessels in the surgical field, the adoption of such systems and methods would be impeded if these systems and methods made the surgical procedure more complicated. As mentioned above, the surgeon often would determine the presence and/or characteristics of vessels in the surgical field by direct visualization and/or touch. As such, the surgeon was able to perform several tasks simultaneously by relying on different senses to obtain different information: some information might be obtained visually, other information by touch. By eliminating the surgeon's ability to directly visualize and interact with the surgical field by touch, minimally invasive surgery not only eliminates the ability of the surgeon to use touch to locate, for example, vessels in the surgical field, but to the extent that this information is presented to the surgeon visually, it must compete with all of the other visual tasks that the surgeon must perform for the surgery to be a success. Consequently, if the information were to be provided visually, it would be advantageous if the information were to be provided without the need for an additional video display to be added to the already cluttered bank of equipment that the surgeon or surgical team must monitor during a procedure.

As set forth in more detail below, the present disclosure describes a user interface embodying advantageous alternatives to the existing systems and methods, which may provide for improved identification for avoidance or isolation of artifacts, such as vessels, without undue complication of the surgical instrument or surgical procedure.

SUMMARY

According to an aspect of the present disclosure, a surgical system includes a shaft having a distal end and a proximal end, the proximal end including a grip, a sensor attached to the distal end of the shaft, at least one visual indicator disposed at the distal end of the shaft, and a controller coupled to the sensor and the at least one visual indicator, the controller actuating the at least one visual indicator according to a signal received from the sensor.

BRIEF DESCRIPTION OF THE DRAWINGS

The disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings is necessarily to scale.

Figure 1:
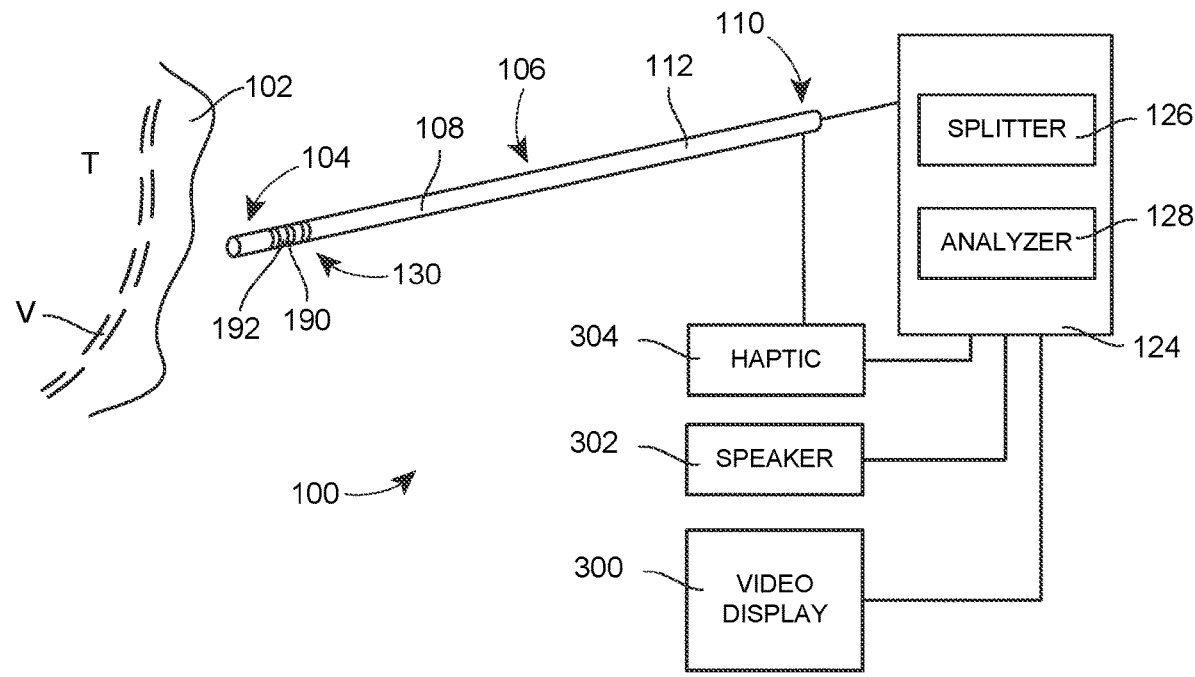
FIG. 1 is a schematic diagram of a surgical system according to an embodiment of the present disclosure.
Figure 3:
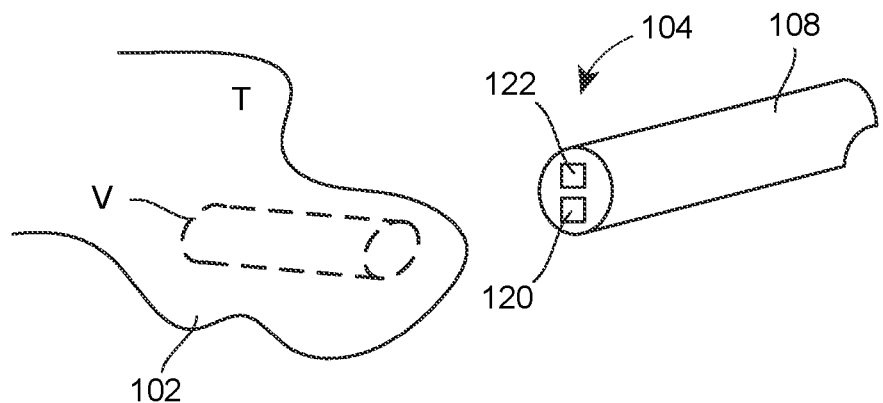
FIG. 3 is an enlarged, fragmentary view of a reflectance-based embodiment of the surgical instrument of FIG. 1 with light emitter and light sensor with fixed spacing, and a section of a vessel illustrated as proximate the light emitter and light sensor.
Figure 5:
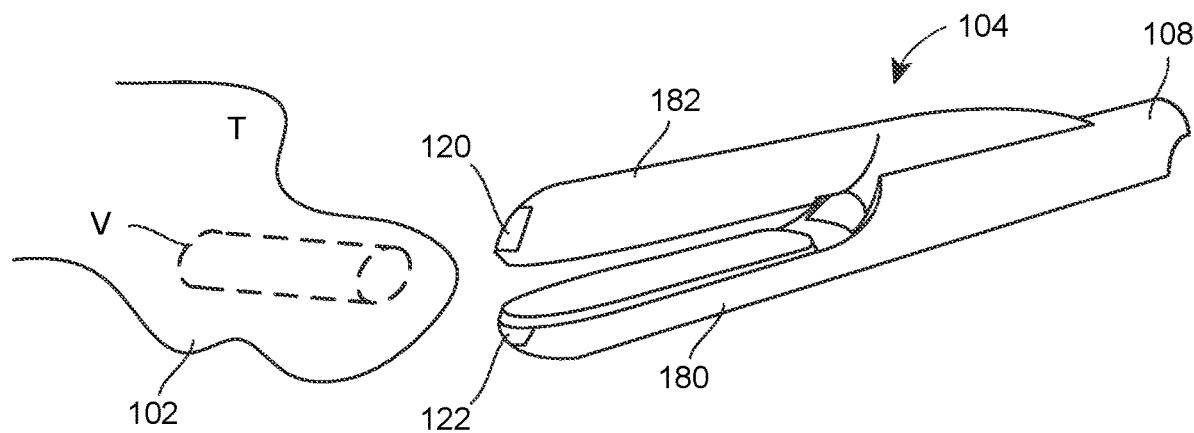
FIG. 5 is an enlarged, fragmentary view of another reflectance-based embodiment of the surgical instrument of FIG. 2 with light emitter and light sensor having an adjustable spacing relative to each other, and a section of a vessel illustrated as proximate the light emitter and light sensor.
Figure 7:
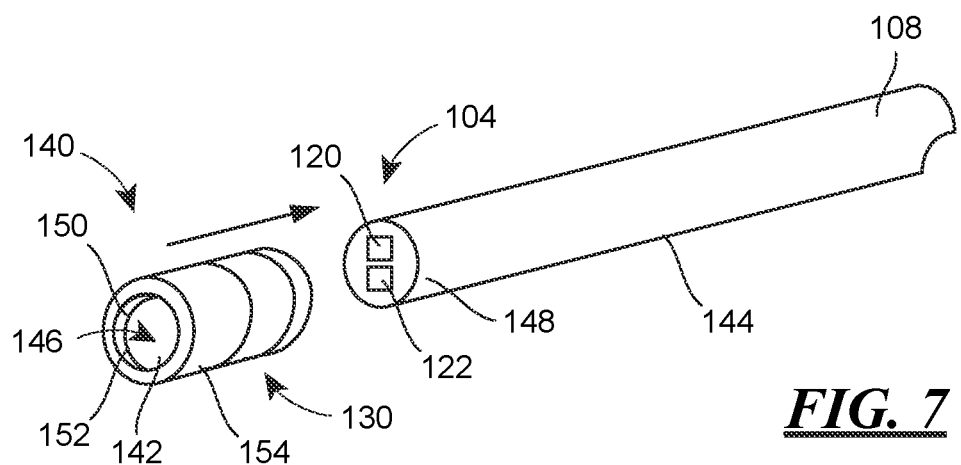
Figure 8:
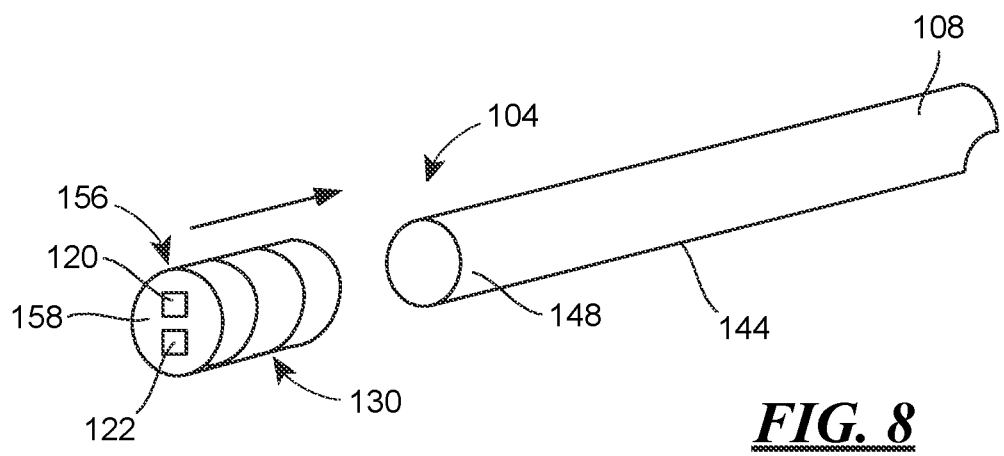
Figure 9:
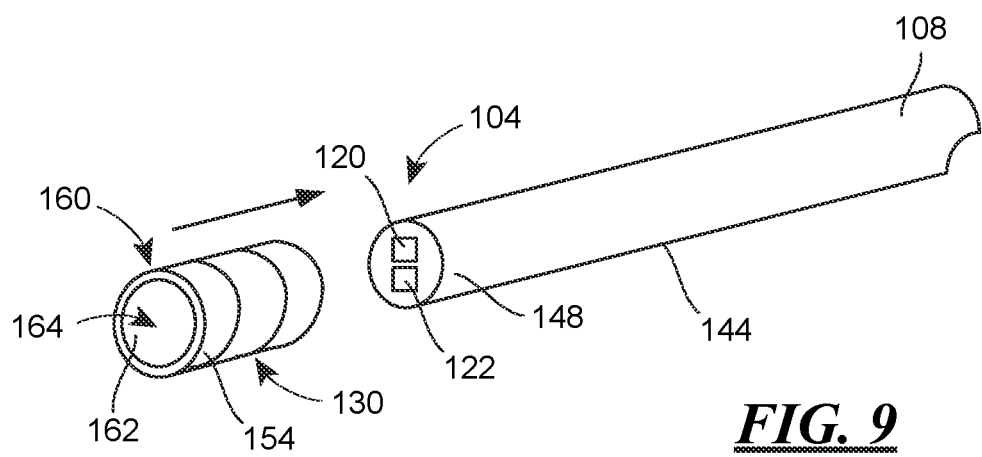
Figure 10:
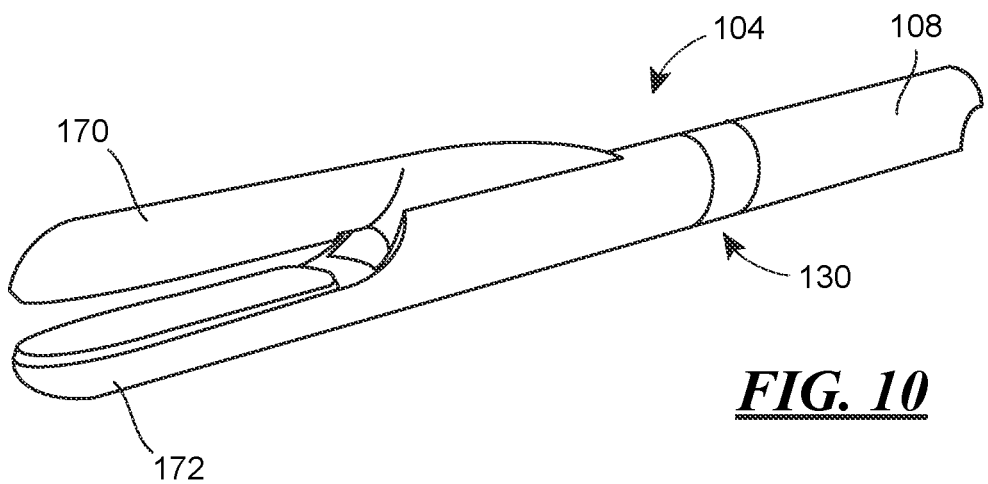
Figure 11:
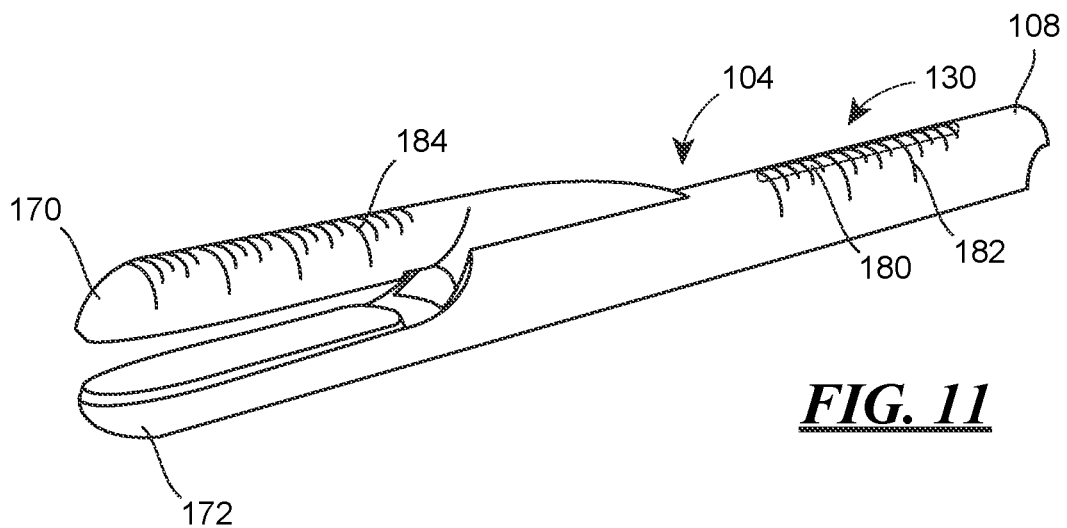
Figure 12:
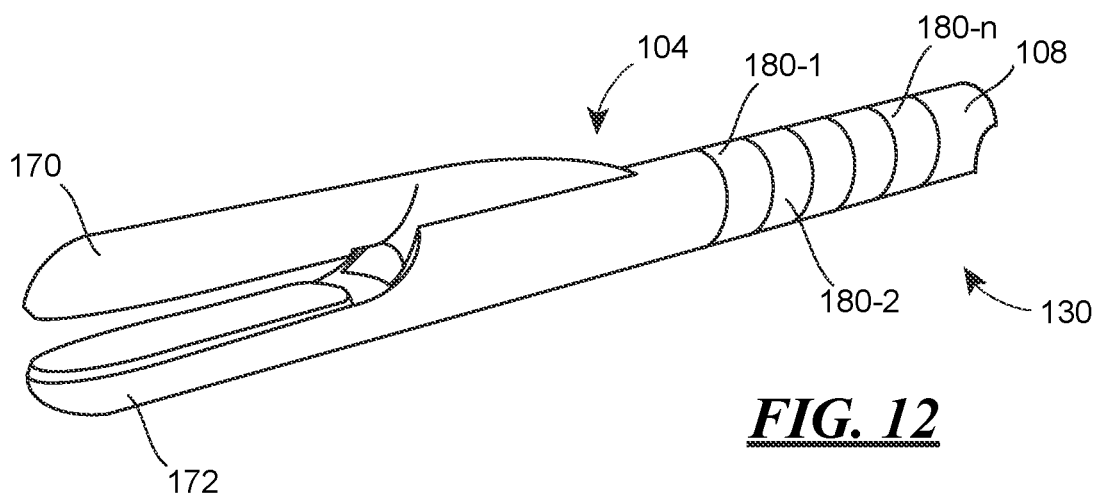
Figure 13:
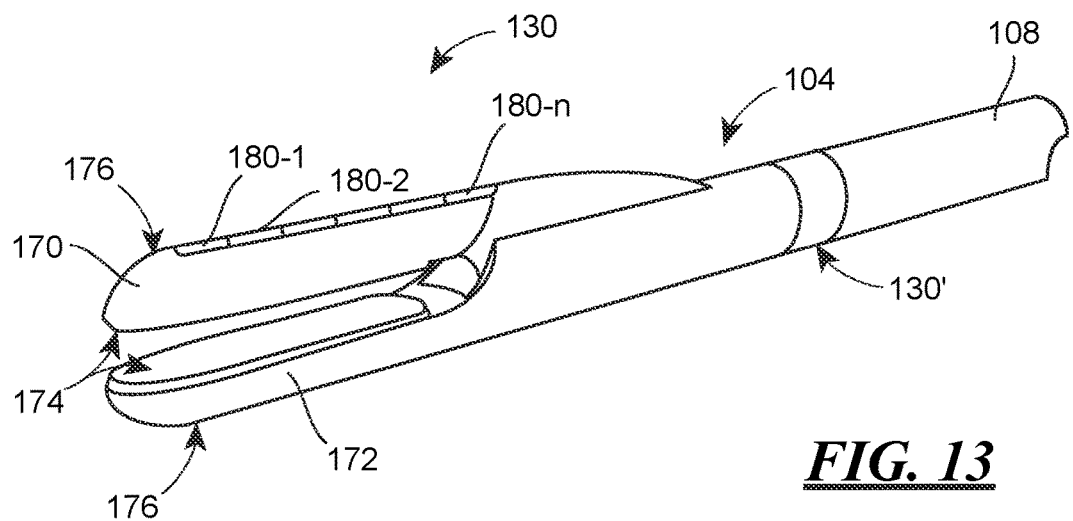
Figure 14:
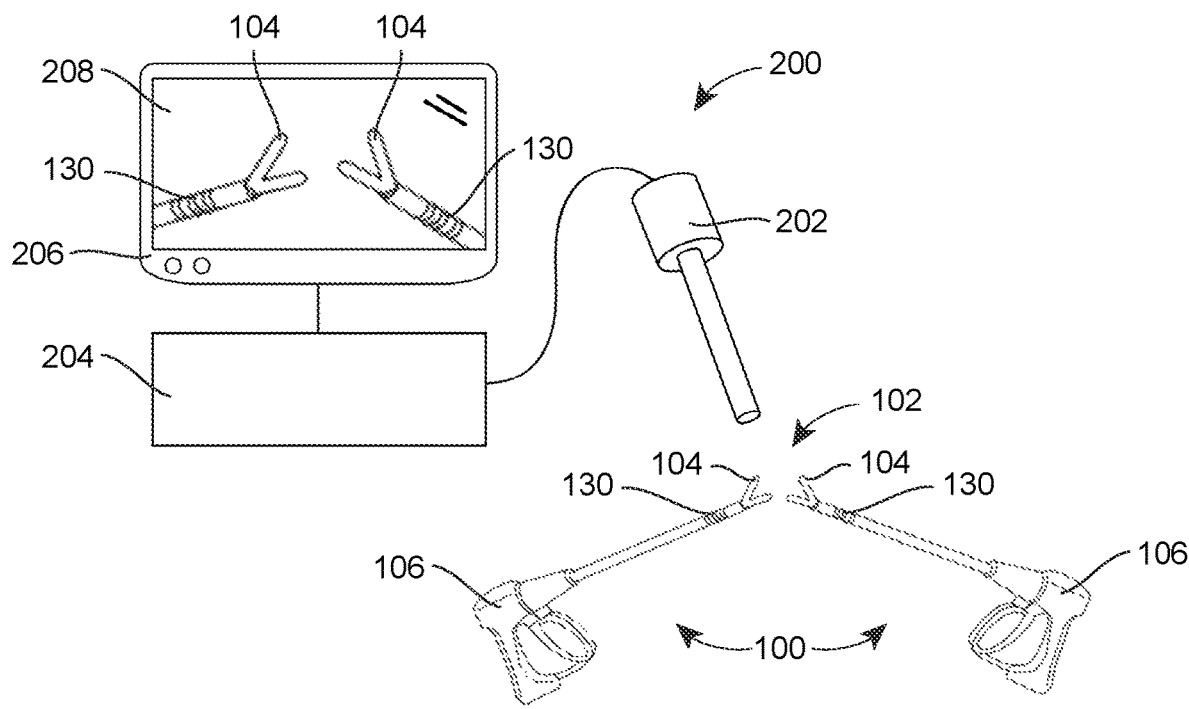
Figure 15:
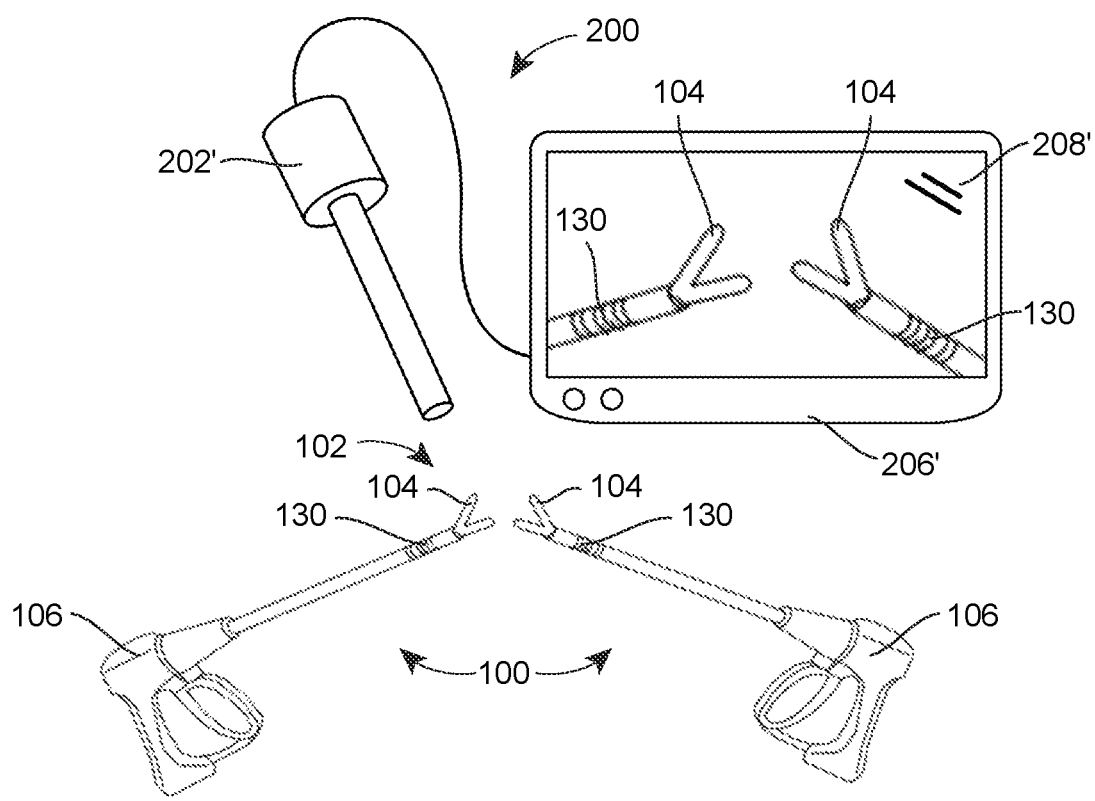

2 with light emitters and light sensors, and a section of a vessel illustrated as disposed between the light emitters and light sensors;

FIG. 7 is an enlarged, fragmentary perspective view of an embodiment of a user interface as incorporated into the embodiment of FIGS. 1 and 3, for example;

FIG. 8 is an enlarged, fragmentary perspective view of an embodiment of another user interface as incorporated into the embodiment of FIGS. 1 and 3, for example;

FIG. 9 is an enlarged, fragmentary perspective view of an embodiment of a further user interface as incorporated into the embodiment of FIGS. 1 and 3, for example;

FIG. 10 is an enlarged, fragmentary perspective view of an embodiment of a user interface as incorporated into the embodiment of FIG. 5, for example;

FIG. 11 is an enlarged, fragmentary perspective view of further embodiments of a user interface as incorporated into the embodiment of FIG. 5, for example;

FIG. 12 is an enlarged, fragmentary perspective view of yet another embodiment of a user interface as incorporated into the embodiment of FIG. 5, for example;

FIG. 13 is an enlarged, fragmentary perspective view of a still further embodiment of a user interface as incorporated into the embodiment of FIG. 5, for example;

FIG. 14 is a schematic diagram of a surgical system according to a an embodiment of the present disclosure, in combination with an embodiment of a video system, illustrating the surgical system in use with the video system; and FIG. 15 is a schematic diagram of a surgical system according to an embodiment of the present disclosure, in combination with another embodiment of a video system, illustrating the surgical system in use with the video system.

DETAILED DESCRIPTION OF VARIOUS EMBODIMENTS

The embodiments described herein provide user interfaces for use with or in systems used to determine characteristics of tissue and/or artifacts in a surgical field. For example, the surgical system may include a shaft having a distal end and a proximal end, the proximal end including a grip or handle. The system may also include a sensor attached to the distal end of the shaft, and at least one visual indicator also disposed at the distal end of the shaft. A controller may be coupled to the sensor and the at least one visual indicator, the controller actuating the at least one visual indicator according to a signal received from the sensor.

By thus positioning the visual indicator, the system displays the information obtained from the sensor such that the information is in close physical proximity to the portion of the surgical field from which the information was obtained. This may simplify the surgeon's or surgical team's processing of this information in one or more of a number of different ways. For example, by positioning the visual indictor at the distal end of the shaft, the visual indictor is disposed in such a way as to be viewable by the surgeon using whatever equipment the surgeon is already using to visualize the surgical field. This would be of benefit where, as in minimally invasive and robotic surgery, the surgical field is being displayed on a monitor connected to a camera or other optical instrument (see, e.g., FIGS. 14 and 15), but could even be of benefit where the surgeon is capable of visualizing the surgical field directly with their eyes. Further, because the surgeon is already focusing their attention on the surgical field as part of the procedure being performed, the display of the information in this manner does not require the surgeon to direct their attention away from the surgical field.

The afore-mentioned shaft may be part of a surgical instrument that is used by the surgeon as part of the procedure, or it may be part of a surgical instrument that is used solely to inspect or survey the surgical field. Considering that the user interface is intended for use in minimally invasive and robotic surgeries, there are advantages that may be obtained if the user interface is integrated with equipment that will also be used in performing the procedure. However, to the extent that the surgeon wishes to inspect an area without moving a surgical instrument that is being used as part of the procedure, to minimize the potential for interaction between the surgical instrument and the area being inspected for example, the user interface could be integrated into a surgical instrument that is used simply for purposes of investigating the surgical field.

According to preferred embodiments, the sensor is a light-based sensor, typically including a light emitter and light sensor that are both coupled to the controller. According to certain embodiments, the light sensor may be coupled to the controller, but the light may be emitted by equipment that is not connected to the controller. The light emitter and light sensor may be disposed opposite each other in a transmittance-based configuration, or the light emitter and light sensor may be disposed generally in the same direction in a reflectance-based configuration. Thus, the specific embodiments described below are for purposes of explanation, and not by way of limitation.

Turning first to FIGS. 1-6, embodiments of a surgical system 100 are illustrated, which system 100 may be used to determine, for example, a characteristic (e.g., presence, diameter, etc.) of a vessel, V, within a region 102 of tissue, T, proximate to a working end 104 of a surgical instrument 106. It will be understood that the vessel V may be connected to other vessels with the region 102 of tissue T, and in addition, the vessel V may extend beyond the region 102 so as to be in fluid communication with other organs (e.g., the heart) also found in the body of the patient. Furthermore, while the tissue T appears in FIGS. 1-6 to surround fully the vessel V (in terms of both circumference and length) to a particular depth, this need not be the case in all instances where the system 100 is used. For example, the tissue T may only partially surround the circumference of and/or only surround a section of the length of the vessel V, or the tissue T may overlie the vessel V in a very thin layer. As further non-limiting examples, the vessel V may be a blood vessel, and the tissue T may be connective tissue, adipose tissue and/or liver tissue.

According to the illustrated embodiments, the working end 104 of the surgical instrument 106 is also a distal end of a shaft 108. Consequently, the working end and the distal end will be referred to as working end 104 or distal end 104. The shaft 108 also has a proximal end 110, and a grip or handle 112 (referred to herein interchangeably as grip 112) is disposed at the proximal end 110 of the shaft 108. The grip 112 is designed in accordance with the nature of the instrument 106; as to the dissector illustrated in FIG. 1, the grip 112 may be defined along a length of the shaft 108, while as to the thermal ligation device illustrated in FIG. 2, the grip 112 may be a pistol-type grip including a trigger 114. As a further alternative, finger rings arranged in a generally scissors-type grip may be used.

While the working or distal end 104 and the proximal end 110 with grip 112 are illustrated as disposed at opposite-most ends of the shaft 108, it will be recognized that certain surgical instruments have working ends (where a tool tip is attached, for example) disposed on the opposite-most ends of the shaft and a gripping region disposed intermediate to the opposite working ends. In accordance with the terms "distal" and "proximal" as used herein, the working ends of such an instrument are referred to herein as the distal ends and the gripping region as the proximal end. Relative to the illustrated embodiments, however, the distal and proximal ends are located at opposite-most (or simply opposite) ends of the shaft 108.

As mentioned above, according to the preferred embodiments illustrated, the surgical system 100 includes a sensor with at least one light emitter 120 (or simply the light emitter 120) and at least one light sensor or detector 122 (or simply the light sensor 122). See FIGS. 3-6. According to the illustrated embodiments, a controller 124 is coupled to the light emitter 120 and the light sensor 122, which controller 124 may include a splitter 126 and an analyzer 128 as explained below. See FIGS. 1 and 2.

Figure 4:
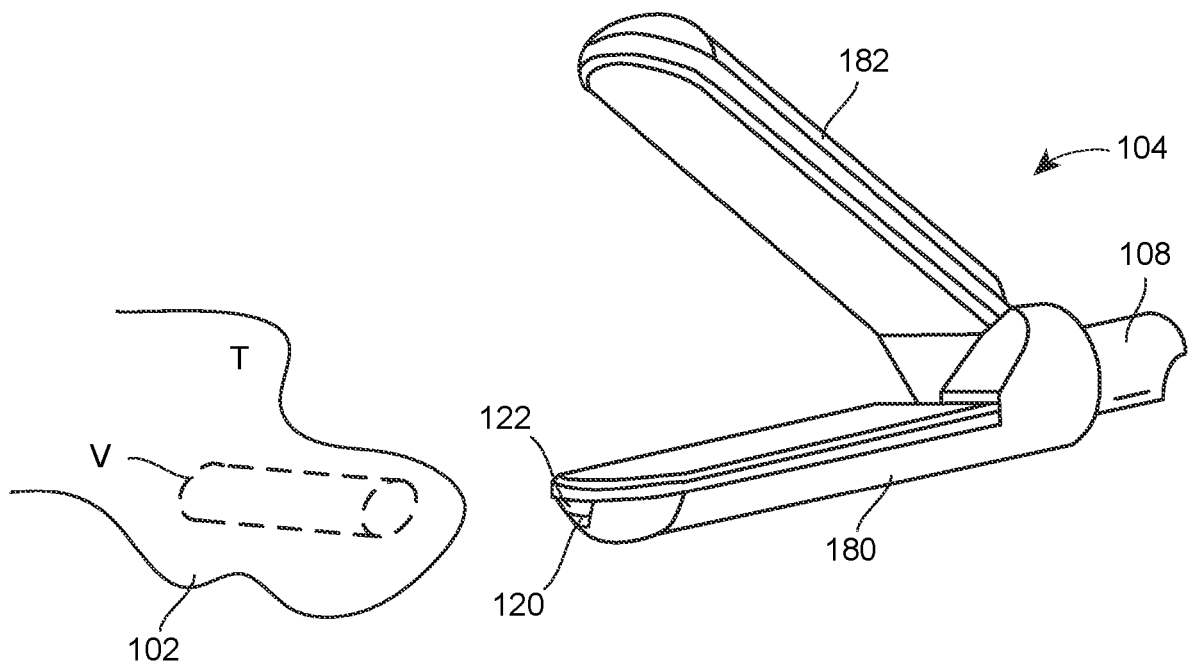
FIG. 4 is an enlarged, fragmentary view of a reflectance-based embodiment of the surgical instrument of FIG. 2 with light emitter and light sensor with fixed spacing, and a section of an vessel illustrated as proximate the light emitter and light sensors.
Figure 6:
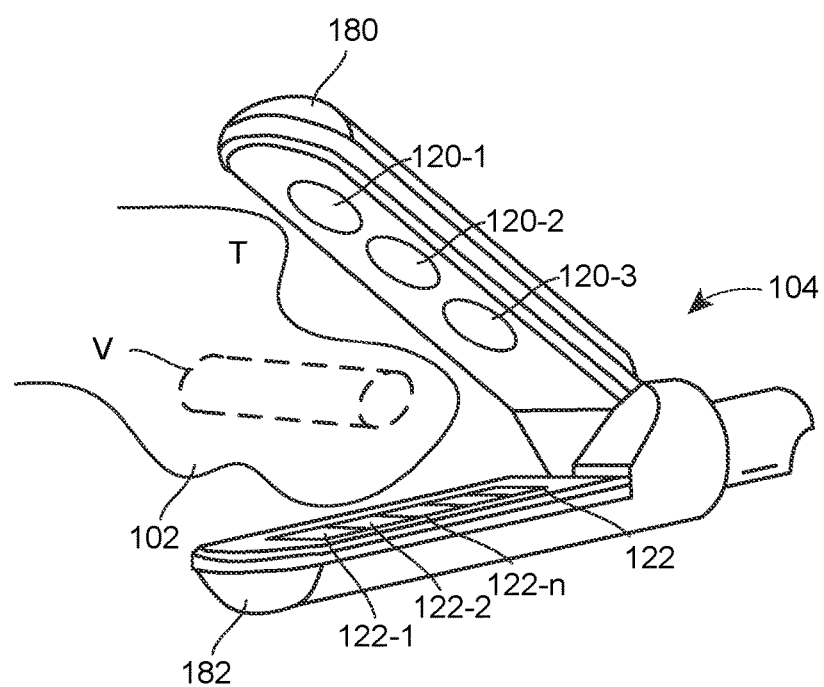
FIG. 6 is an enlarged, fragmentary view of a transmittance-based embodiment of the surgical instrument of FIG.

The light emitter 120 is disposed at the working end 104 of the surgical instrument 106. The light sensor 122 is also disposed at the working end 104 of the surgical instrument 106. As illustrated in FIGS. 3 and 4, the system 100 may operate according to a reflectance-based approach, such that the light emitter 120 and the light sensor 122 may face in a common direction and with fixed spacing therebetween, for example on a blunt end of a laparoscopic dissection tool or dissector (FIG. 3) or on a single jaw of a two-jaw device, such as a thermal ligation device (FIG. 4), although the relative angle between the light emitter 120 and light sensor 122 may be fixed or variable. The light emitter 120 and the light sensor 122 of a reflectance-based system may be constructed such that the spacing between the light emitter 120 and the light sensor 122 may be adjusted, for example by positioning the light emitter 120 at the end or tip of one of the jaws of a two jaw device and the light sensor 122 at the end or tip of the other the jaws of the two jaw device, as illustrated in FIG. 5. Alternatively, the system 100 may operate according to a transmittance-based approach, such that the light sensor(s) 122 is/are disposed opposite and facing the light emitter(s) 120, for example on opposite jaws of a surgical instrument 106 as illustrated in FIG. 6.

The light emitter 120 may be adapted to emit light of at least one wavelength. For example, the light emitter 120 may emit light having a wavelength of 660 nm. This may be achieved with a single element, or a plurality of elements (which elements may be arranged or configured into an array, for example, as explained in detail below). In a similar fashion, the light sensor 122 is adapted to detect light at the at least one wavelength (e.g., 660 nm). According to the embodiments described herein, the light sensor 122 includes a plurality of elements, which elements are arranged or configured into an array.

According to certain embodiments, the light emitter 120 may be configured to emit light of at least two different wavelengths, and the light sensor 122 may be configured to detect light at the at least two different wavelengths. As one example, the light emitter 120 may emit and the light sensor 122 may detect light in the visible range and light in the near-infrared or infrared range. Specifically, the light emitter 120 may emit and the light sensor 122 may detect light at 660 nm and at 910 nm. Such an embodiment may be used, for example, to ensure optimal penetration of blood vessel V and the surrounding tissue T under in vivo conditions.

Depending upon the effect of changes in blood flow, light of a third wavelength may also be emitted and sensed. That is, if the method of detection is found to be sensitive to varying rates of blood flow in the vessel of interest, light at 810 nm (i.e., at the isobestic point) may be emitted and sensed to permit normalization of the results to limit or eliminate the effects of changes in blood flow rate.

According to some embodiments, the individual light sensor 122 is adapted to generate a signal comprising a first pulsatile component and a second non-pulsatile component. It will be recognized that the first pulsatile component may be an alternating current (AC) component of the signal, while the second non-pulsatile component may be a direct current (DC) component. Where the light sensor 122 is in the form of an array, the pulsatile and non-pulsatile information may be generated for each element of the array, or at least for each element of the array that defines the at least one row of the array.

As to the pulsatile component, it will be recognized that a blood vessel may be described as having a characteristic pulsation of approximately 60 pulses (or beats) per minute. While this may vary with the patient's age and condition, the range of pulsation is typically between 60 and 100 pulses (or beats) per minute. The light sensor 122 will produce a signal (that is passed to the controller 124) with a particular AC waveform that corresponds to the movement of the blood through the vessel. In particular, the AC waveform corresponds to the light absorbed or reflected by the pulsatile blood flow within the vessel. On the other hand, the DC component corresponds principally to light absorbed, reflected and/or scattered by the superficial tissues.

According to such embodiments, the controller 124 is coupled to the light sensor 122, and may include a splitter 126 to separate the first pulsatile component from the second non-pulsatile component for each element of the light sensor array 122. The controller 124 may also include an analyzer 128 to determine the presence of and/or characteristic(s) of the vessel V within the region 102 proximate to the working end 104 of the surgical instrument 106 based (at least in part) on the pulsatile component.

Figure 2:
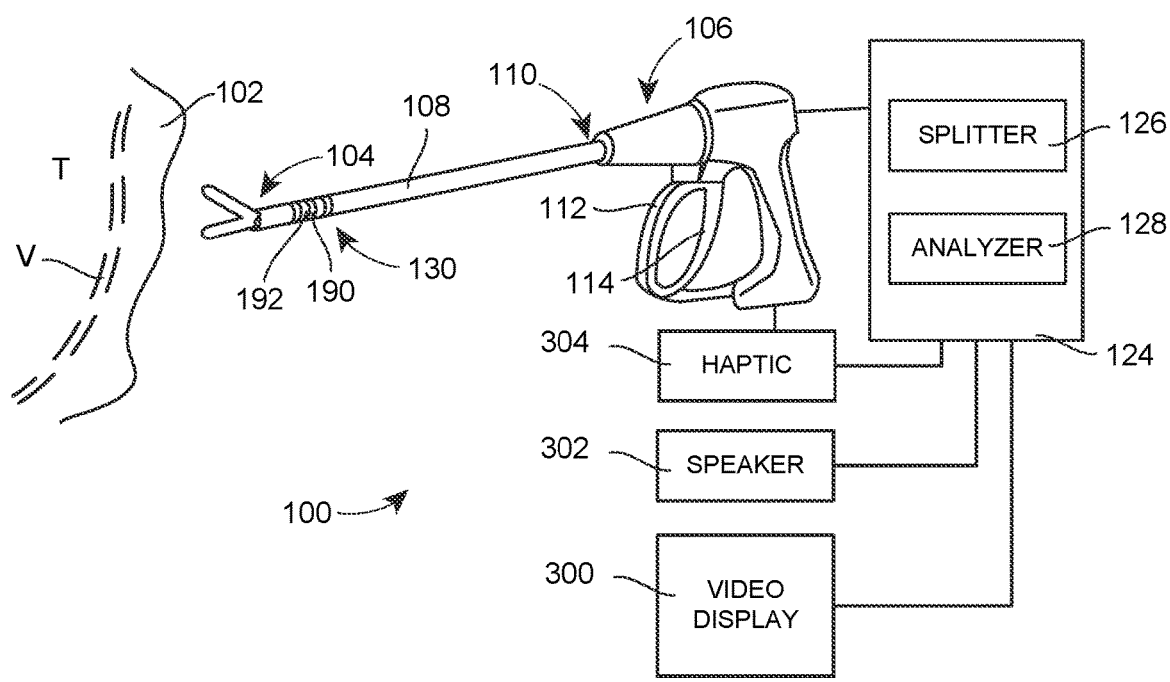
FIG. 2 is a schematic diagram of a surgical system according to another embodiment of the present disclosure.

To display, indicate or otherwise convey the size of the vessel V within the region 102, the controller 124 may be coupled to a visual user interface 130 (or user interface 130, for short), which may provide a visible signal to the user of the instrument 106. See FIGS. 1, 2 and 7-13. As stated above, the user interface 130 includes at least one visual indicator disposed at the distal end 104 of the shaft 108, which at least one visual indicator may also be referred to generally as 130. As illustrated in FIGS. 1, 2, the at least one visual indicator 130 is coupled to the controller 124, and the controller 124 actuates the at least one visual indicator according to a signal received from the sensor 120/122 as explained in greater detail below.

As to the user interface 130, according to some embodiments, the at least one visual indicator is attached to the distal end of the shaft. As to such embodiments, the system may include an adapter attached to the distal end of the shaft, the at least one visual indicator disposed on the adapter. See, e.g., FIGS. 7-9. In a similar fashion, the system may include first and second jaws attached to the distal end of the shaft, and the at least one visual indicator is disposed on at least one of the first and second jaws. See, e.g., FIG. 13. According to some embodiments, the at least one visual indicator is integral with the distal end of the shaft. See, e.g., FIGS. 1, 2, and 10-12.

As mentioned above, the user interface 130 may include at least one visual indicator. The at least one visual indicator may include at least one light emitting element, such as a light emitting diode. The visual indicator may also include a light transmitting element that carries and/or directs light emitted by the light emitting element for display at a point remote to the light emitting element (e.g., a light guide such as fiber optic cable or band).

Where more than one visual indicator is provided, the visual indicator may include an array of visual indicators, and when the visual indictor includes more than one light emitting element, the light emitting elements may include an array of light emitting elements. Furthermore, such an array of visual indicators or light emitting elements may be continuous or discontinuous. Where the elements are discontinuous, the visual indicator may include spacers disposed between the individual elements of the array.

The visual indicator may provide light of one or more colors within the visible spectrum, and may provide the light in a continuous or discontinuous (e.g., pulsing, flashing, shifting, etc.) manner. As another embodiment, the visual indicator may provide light of different intensities, and may provide that light of different intensities in a continuously or discontinuously varying or changing manner. In particular, where an array of visual indicators or light emitting elements is provided, different individual indicators or elements may provide light of different colors or intensities, or alternatively may provide continuous or discontinuous light. For example, a first element of an array of visual indicators may provide a continuous light (for example, to represent that a vessel is within a first range of the sensor) while a second element of the array may provide discontinuous light (for example, a flashing light, to represent that a vessel is within a second range of the sensor that is smaller than the first range). As a further example, light emitting elements of different colors may indicate the presence of different types of tissue (e.g., blood vessel, connective tissue, adipose tissue, etc.), as might a change in from continuous to discontinuous light or a change in the rate of pulsing of discontinuous light. According to still other embodiments, the light may be directed so that it is visible to the surgeon as he views the light emitting elements; according to further embodiments, the light may be directed onto the tissues or structures surrounding the instrument so that the region 102 may appear to be illuminated with one color of light or another.

Having thus described the visual user interface 130 in general terms, the embodiments of FIGS. 7-13 are discussed in detail.

FIG. 7 illustrates an embodiment of a user interface 130 that is attached to the distal end 104 of the shaft 108. In particular, the system 100 includes an adapter 140 that is attached to the distal end 104 of the shaft 108, and the visual indicator 130 is disposed on the adapter 140. In particular, the shaft 108 has a cylindrical cross-section, and the adapter 140 is disposed about the cylindrical cross-section of the shaft 108. In particular, the adapter 140 has a wall with an inner surface 142, and an inner diameter of the adapter 140 bounded by the inner surface 142 is selected to be larger than the outer diameter bounded by an outer surface 144 of the shaft 108. The degree to which the inner diameter of the adapter 140 is larger than the outer diameter of the shaft 108 is a matter of design choice, and may be influenced by the selection of the mechanism for attachment between the adapter 140 and the shaft 108 (e.g., friction fit, adhesive, etc.). In addition, it will be recognized that where the shaft 108 (or at least the distal end 104 of the shaft 108) is non-cylindrical, the dimensions bounded by the inner surface 142 of the adapter 140 may be selected to accommodate the dimensions bounded by the outer surface 144 of the shaft 108.

As to the illustrated embodiment of FIG. 7, a light emitter 120 and a light sensor 122 are disposed on the distal end 104 of the shaft 108. Consequently, the adapter 140 includes an opening 146 that permits the light emitter 120 and the light sensor 122 to emit and receive light while the adapter 140 is disposed on the distal end 104 of the shaft 108. To limit the movement of the adapter 140 relative to a distalmost tip 148 of the shaft 108, a rim 150 is disposed about the periphery of the opening 146. With reference to the illustrated embodiment, the rim 150 defines an inner diameter that is smaller than the inner diameter bounded by the inner surface 142 of the adapter 140, such that the shaft 108 cannot pass through the opening 146 (i.e., the rim 150 prevents the shaft 108 from being disposed through both a proximal and a distal end of the adapter 140). As such, the adapter 140 is mounted on the distal end 104 of the shaft 108, and in particular on the distalmost tip 148 of the shaft 108. As illustrated, if the adapter 140 is advanced in the direction of the arrow, the distalmost tip 148 of the shaft 108 would abut a shoulder 152 defined by the rim 150.

The user interface 130 of the embodiment of FIG. 7 may be coupled to the controller 124 using a number of different mechanisms. For example, a wire could run from the adapter 140 along the outside of the shaft 108 to the controller 124. Alternatively, the distal end 104 of the shaft 108 may have an electrical contact disposed on the outer surface 144 of the shaft 108, which electrical contact is brought into alignment and contact with an electrical contact disposed on the inner surface 142 of the adapter 140 when the adapter 140 is mounted on the distal end 104. Other alternative mechanisms are possible.

As illustrated, the visual indicator 130 may be in the form of a band that is disposed about the periphery of an outer surface 154 of the adapter 140. The band may be defined by a plurality of light emitting elements, such as light emitting diodes, disposed on or integrally with the outer surface 154 of the adapter. Alternatively, a single light emitting element may be included, but with a light carrier or reflector that distributes the light from the light emitting element about the periphery of the adapter 140. Again, other embodiments for the visual indicator 130 are possible.

According to an exemplary mode of operation, the visual indicator 130 may be activated by the controller 124 when a vessel V is within a certain range of the distalmost tip 148 of the shaft 108. As an alternative mode of operation, the visual indicator 130 may be activated by the controller 124 when a vessel V is within a first range of the distalmost tip 148 of the shaft 108, and the controller 124 may cause the visual indicator 130 to flash or pulse if the distalmost tip 148 of the shaft 108 moves closer to the vessel than the first range. As a further alternative, the controller 124 may cause the visual indicator 130 to flash or pulse at different rates dependent upon the distance between the distalmost tip 148 of the shaft 108 and the vessel. As still another alternative, the controller 124 may cause the visual indicator 130 to emit light of a first color (e.g., green) when no vessel is detected within a first distance of the sensor, to emit light of a second color (e.g., yellow) when a vessel is detected within a second (smaller) distance of the sensor and to emit a light of third color (e.g., red) when a vessel is detected within a third (still smaller) distance of the sensor. According to yet another alternative, the controller 124 may cause the color of light to shift between, for example, green, yellow and red as the sensor detects that the distalmost tip 148 of the shaft 108 is being brought closer to a vessel.

FIG. 8 illustrates another embodiment of a user interface 130 that is attached to the distal end 104 of the shaft 108, and like the embodiment of FIG. 7, the system 100 includes an adapter 156 that is attached to the distal end 104 of the shaft 108, and the visual indicator 130 is disposed on the adapter 156. In addition, similar to the embodiment of FIG. 7, the shaft 108 has a cylindrical cross-section, and the adapter 156 is disposed about the cylindrical cross-section of the shaft 108. Unlike the embodiment of FIG. 7, the adapter has a closed end 158 on which the light emitter 120 and the light sensor 122 are mounted. Thus, the light emitter 120, light sensor 122, and the indicator 130 are disposed on the adapter 156, and the shaft 108 thus would need to have a connection or connections for the light emitter 120, light sensor 122, and indicator 130 or some other form of connection or coupling would need to be provided.

Similar to the embodiment of FIG. 7, the adapter 156 of FIG. 8 has a wall with an inner surface, and an inner diameter of the adapter 156 of FIG. 8 bounded by the inner surface is selected to be larger than the outer diameter bounded by an outer surface 144 of the shaft 108. Similar to the embodiment in FIG. 7, the degree to which the inner diameter of the adapter 156 is larger than the outer diameter of the shaft 108 is a matter of design choice, and may be influenced by the selection of the mechanism for attachment between the adapter 156 and the shaft 108 (e.g., friction fit, adhesive, etc.). In addition, it will be recognized that where the shaft 108 (or at least the distal end 104 of the shaft 108) is non-cylindrical, the dimensions bounded by the inner surface of the adapter 156 may be selected to accommodate the dimensions bounded by the outer surface 144 of the shaft 108.

The further comments made about the visual indicator 130 and the mode of operation of the visual indicator 130 relative to the embodiment of FIG. 7, above, apply with equal force to the embodiment of FIG. 8.

FIG. 9 illustrates another embodiment of a user interface 130 that is attached to the distal end 104 of the shaft 108, and like the embodiment of FIG. 7, the system 100 includes an adapter 160 that is attached to the distal end 104 of the shaft 108, and the visual indicator 130 is disposed on the adapter 160. In addition, similar to the embodiment of FIG. 7, the shaft 108 has a cylindrical cross-section, and the adapter 160 is disposed about the cylindrical cross-section of the shaft 108. Unlike the embodiment of FIG. 7, the embodiment of FIG. 9 does not include a rim, such that the distal end 104 of the shaft 108 (and in particular the distalmost tip 148 of the shaft 148) is received through proximal and distal ends of the adapter 160. The adapter 160 may thus be disposed along the shaft 108 at the distal end 104, but without being mounted on the distalmost top of the shaft 108. The system 100 may include a mechanism for ensuring a certain position of the adapter 160 relative to the shaft 108, but this may be in the form of a shoulder disposed along the length of the shaft 108, for example.

As illustrated, the adapter 160 has a wall with an inner surface 162, and an inner diameter of the adapter 160 bounded by the inner surface 162 is selected to be larger than the outer diameter bounded by an outer surface 144 of the shaft 108. Similar to the embodiment in FIG. 7, the degree to which the inner diameter of the adapter 160 is larger than the outer diameter of the shaft 108 is a matter of design choice, and may be influenced by the selection of the mechanism for attachment between the adapter 160 and the shaft 108 (e.g., friction fit, adhesive, etc.). In addition, it will be recognized that where the shaft 108 (or at least the distal end 104 of the shaft 108) is non-cylindrical, the dimensions bounded by the inner surface 162 of the adapter 160 may be selected to accommodate the dimensions bounded by the outer surface 144 of the shaft 108.

The further comments made about the visual indicator 130 and the mode of operation of the visual indicator 130 relative to the embodiment of FIG. 7, above, apply with equal force to the embodiment of FIG. 9. Furthermore, while the embodiment of FIG. 9 has been discussed relative to a shaft 108 in which the light emitter/sensor pair 120, 122 is disposed at the distalmost tip 148 of the shaft 108, it will be recognized that the embodiment of FIG. 9 may be used to mount the visual indicator 130 on any shaft 108, for example one that has a two jawed mechanism attached thereto, as illustrated for example in FIGS. 4-6. According to such an embodiment, the adapter 160 may be moved along the shaft 108 from the opposite end 110 of the shaft 108 (before or after assembly of the two jaw mechanism with the shaft 108), or the adapter 160 may have a discontinuity (e.g., a slit or slot) running along its longitudinal length, which discontinuity may permit the adapter 160 to be deflected sufficiently to accept the shaft 108 within the space bounded by the inner surface 162 before the adapter returns to its undeflected shape.

For purposes of comparison, FIG. 10 illustrates an embodiment of a user interface 130 that is integral with the distal end 104 of the shaft 108. The embodiment of FIG. 10 also differs from that of FIGS. 7-9 in that the shaft 108 does not terminate in a blunt end, but instead two jaws 170, 172 are disposed at the distal end 104, at least one of the jaws having a sensor disposed thereon and attached thereto or formed integrally therewith. In fact, the sensor may include a light sensor and a light emitter, the light emitter also disposed on at least one of the first and second jaws. In certain embodiments, the light emitter is attached to the first jaw and the light sensor is attached to the second jaw, as in FIGS. 5 and 6, but both emitter and sensor may be attached to a single jaw, as in FIG. 4. It will be recognized, however, that while the embodiment of FIG. 10 includes jaws 170, 172, it is not necessary that an embodiment where the interface 130 is integral with the distal end 104 of the shaft 108 should include the jaws 170, 172. Thus, the user interface according to FIG. 10 could be incorporated into a system such as is illustrated in FIGS. 1 and 3 as well. This interchangeability applies relative to the embodiments of FIGS. 10 and 12 as well.

As was the case with the embodiment of FIGS. 8 and 9, the comments made regarding the visual indicator 130 and its mode of operation in the embodiment of FIG. 7 apply equally to the embodiment of FIG. 10.

FIG. 11 also illustrates an embodiment of a user interface 130 that is integral with the distal end 104 of the shaft 108. In particular, the visual indicator 130 stretches along a portion of the shaft 108 parallel to the longitudinal axis of the shaft 108, as illustrated in FIG. 11. This is a different orientation for the visual indicator 130 than the radial, banded or annular arrangement illustrated in FIGS. 7-10, although it will be appreciated that the embodiment of visual indicator 130 illustrated in FIG. 11 could be incorporated into the embodiments of FIGS. 7-9 as well (i.e., disposed on the adapter 140 or 160). The visual indicator 130 may include an array of light emitting elements (e.g., light emitting diodes) 180, or may include a single light emitting element capable of partial and/or total illumination along the length of the visual indicator 130.

As illustrated, a plurality of visible line segments 182 are disposed over the light emitting region of the visual indicator 130 transverse to the length of the visual indicator 130. The visible line segments 182 need not be disposed over the light emitting elements 180, but may be disposed adjacent the light emitting elements 180 according to other embodiments. Certain of the line segments 182 may extend to a greater degree or length to either side of the light emitting elements 180 than other of the line segments 182; in fact, the visible line segments 182 may be of at least three different lengths in the transverse direction as illustrated in FIG. 11. The visible line segments 182 may be combined with alphanumeric indicia, such as may be found on a ruler or scale, to provide an indication of distance between two points.

The combination of the visible line segments 182 with the light emitting elements 180 in the embodiment of the visual indicator 130 of FIG. 11 may provide for a number of different modes of operation. For example, one or more of the light emitting elements 180 or one or more portions of a single light emitting element 180 may be activated to represent, in conjunction with the visible line segments 182, the distance between the distalmost tip of the shaft 108 (or as illustrated, the distalmost tip of the jaws 170, 172) and a vessel in the surgical field. Alternatively, the light emitting element(s) 180 may be successively illuminated once a vessel is present a certain distance from the distalmost end of the instrument 106 to represent a decreasing distance between the working end 104 of the instrument 106 and the vessel.

As a further alternative, as is illustrated in FIG. 11, one or more of the jaws 170, 172 may have a plurality of series of visible line segments 184 disposed thereon (as illustrated, the jaw 170). These line segments 184 may have the same characteristics as those described above relative to the visual indicator 130 (e.g., transverse to the length of the jaw 170, of varying transverse length, associated with alphanumeric indicia, etc.). In fact, the visible line segments 184 on the jaw 170 may have a one-to-one correspondence to the visible line segments 182 on the shaft 108. In this way, the presence of a vessel between the jaws 170, 172 may be represented by illuminating the light emitting element(s) 180 of the visual indicator 130, and the surgeon may be able to directly correlate the display on the visual indicator 130 with the jaws 170, 172.

FIG. 12 illustrates an embodiment of a user interface 130 that is integral with the distal end 104 of the shaft 108. As was the case with the embodiment of FIG. 10, the shaft 108 has two jaws disposed at the distal end 104, but the embodiment could be into a system such as is illustrated in FIGS. 1, 3, and 7-9 as well. This embodiment is similar to that of FIG. 11, in that a visual indicator 130 is disposed along the longitudinal length of the shaft 108, and particularly includes a plurality of light emitting elements (optionally with associated carriers or guides) 180-1, 180-2, . . . 180-$n$. In the specific embodiment illustrated, n=5. Unlike the embodiment of FIG. 11, the visual indicator 130 of FIG. 12 need not include the visible line segments, because the surgeon may use the demarcations between adjacent light emitting elements 180 to judge distances in the same way as they might the visible line segments of FIG. 12. It will be recognized that the embodiment of FIG. 12 has an advantage over the embodiment of FIG. 11 in that the visual indicator 130 is visible regardless of the orientation of the shaft 108. To further enhance the readability of the visual indicator 130, visible line segments such as are include in the embodiment of FIG. 11 may be included in the embodiment of FIG. 12.

While the light emitting elements 180-1 to 180-$n$ may appear to run continuously along the length of the shaft 108, as illustrated in a similar embodiment in FIGS. 1 and 2, light emitting elements 190 may be spaced such that there is a non-light emitting region disposed between adjacent light emitting elements. According to the embodiments illustrated in FIGS. 1 and 2, spacers 192 may be disposed between the light emitting elements 190. The inclusion of spacers 192 between the light emitting elements 190 may assist in making which of the light emitting elements 190 is illuminated at any one time more apparent.

As for the modes of operation of the visual indicator 130 of FIGS. 1, 2, and 12, these may include the modes of operation discussed above relative to FIG. 11. To this end, the jaw 170 of the embodiment of FIG. 12 may include the visible line segments illustrated in FIG. 11 so that a surgeon may correlate the illumination/delumination of the light emitting elements 180-1 to 180-$n$ with the presence of a vessel between the jaws 170, 172, for example. Moreover, the embodiments 1, 2, and 12 may be incorporated into the embodiments of FIGS. 7-9 (i.e., the visual indicators 130 of FIGS. 1, 2, and 12 may be disposed on the adapters 140 and 160).

FIG. 13 illustrates an embodiment of a user interface 130 that is attached to the distal end 104 of the shaft 108, but in a different way that relative to FIGS. 7-9. Specifically, the system 100 may include first and second jaws 170, 172 attached to the distal end 104 of the shaft 108, and the at least one visual indicator 130 is disposed on at least one of the first and second jaws 170, 172 (in this case, jaw 170). More specifically, the first and second jaws 170, 172 each may have a first surface 174 and a second surface 176 on an opposite side of the jaw 170, 172 from the first surface 176, the first surfaces 174 of the first and second jaws 170, 172 facing each other and the at least one visual indicator 130 disposed on the second surface 176 of at least one (170) of the first and second jaws 170, 172. The at least one visual indicator 130 may be attached to or integral (i.e., not detachable and of one piece) with the second surface 176 of the at least one of the first and second jaws 170, 172

As to the nature of the visual indicator 130 of FIG. 13, as illustrated the visual indicator 130 includes a plurality of light emitting elements 180-1 to 180-$n$, with n=6. In fact, the specifics and modes of operation of the embodiment of FIG. 13 may be similar to that of FIG. 11 or 12. It will be recognized that other visual indicators described here may be incorporated into the embodiment of FIG. 13. For that matter, while a single visual indicator 130 is disposed on the jaw 170 of the illustrated embodiment of FIG. 13, a visual indicator 130 may also be disposed on the surface 176 of the jaw 172 as well to increase the readability of the user interface 130.

It will be recognized that more than one visual indicator may be included at the distal end 104 of the shaft 108. As illustrated in FIG. 13, a second visual indicator 130' is included on the shaft 108, in addition to the visual indicator 130 disposed on the jaw 170. The second visual indicator 130' may be used to provide a reinforcement of the information conveyed by the visual indicator 130, or the visual indicator 130' may be used to convey different information that the visual indicator 130. For example, the second visual indicator 130' may be illuminated depending on the presence of a vessel proximate to the jaws 170, 172, while the first visual indicator 130 may be used to display the (approximate) position of the vessel between the jaws 170, 172.

Having discussed various modes of operation of the user interface 130 and its modes of operation, additional details regarding the sensor, the controller and other ancillary equipment are now provided.

While the foregoing user interface 130 may be used with the light emitter 120 and light sensor 122 that together define the sensor, it will be recognized that the user interface may be used with other sensors as well. For example, the user interface 130 may be used with an ultrasonic sensor instead. The most preferred system includes the user interface 130, the light emitter 120 and the light sensor 122, however. Consequently, further comments regarding the light emitter 120 and light sensor 122 are included below.

The light emitter 120 may include one or more elements, as referenced above. According to an embodiment schematically illustrated in FIG. 6, the light sensor 122 may include a first light emitter 120-1, a second light emitter 120-2, and a third light emitter 120-3. All of the light emitters may be adapted to emit light at a particular wavelength (e.g., 660 nm), or certain emitters may emit light at different wavelengths than other emitters. Each light emitter may be a light emitting diode, for example.

As to those embodiments wherein the light emitter 120 is in the form of an array including one or more light emitting diodes, as is illustrated in FIG. 6, the diodes may be arranged in the form of a one-dimensional, two-dimensional or three-dimensional array. An example of a one-dimensional array may include disposing the diodes along a line in a single plane, while an example of a two-dimensional array may include disposing the diodes in a plurality of rows and columns in a single plane. Further example of a two-dimensional array may include disposing the diodes along a line on or in a curved surface. A three-dimensional array may include diodes disposed in more than one plane, such as in a plurality of rows and columns on or in a curved surface.

The light sensor 122 also may include one or more elements. Again, according to the embodiment illustrated in FIG. 6, the light sensor 122 may include a first light sensor 122-1, a second light sensor 122-2, an n-th light sensor 122-n, and so on. As was the case with the light emitters 120-1, 120-2, 120-3, the light sensors 122-1, 122-2, 122-3 may be arranged in an array, and the discussion about the arrays above applied with equal force here.

In fact, where the array of light sensors 122 includes a row of light sensors (such as in FIG. 6), the array 122 may be referred to in the alternative as a linear array. The individual light sensors of the array 122 may be disposed adjacent each other, or the light sensors may be spaced from each other. It may even be possible for the individual light sensors that define a row of light sensors to be separated from each other by light sensors that define a different row or column of the array. According to a particular embodiment, however, the array may comprise a charge coupled device (CCD), and in particular linear CCD imaging device comprising a plurality of pixels. As a further alternative, a CMOS sensor array may be used.

While the arrangement of the light emitter 120 and the light sensor 122 may vary relative to the reflectance-based embodiments of FIGS. 3-5, it is equally true that the light emitter 120 and the light sensor 122 may involve a plurality of elements.

Contrasting the arrangement illustrated in FIGS. 3-5 with that of FIG. 6 then, the light emitter 120 and light sensor 122 are disposed generally facing in a common direction (i.e., the direction of the tissue sample of interest). This does not require the emitter 120 and the sensor 122 to be generally disposed in a common plane, although this is preferred. According to certain embodiments, the emitter 120 and sensor 122 may be formed integrally (i.e., as one piece) with a surgical instrument 106 (see FIGS. 3-5), although other options are possible, as discussed below. In this manner, light emitted by the emitter 120 and scattered by the tissue of interest may be captured by the light sensor 122.

Further, it is believed that the spacing between the emitter 120 and the sensor 122 may influence the light received by the sensor 122. As presently understood, after photons leave the emitter 120 in contact with tissue, an ensemble of independent photons return to the surface and reach the sensor 122. Some of the detected photons travel a short distance from the plane of the emitter and detector and exit at the site of the sensor 122, while some photons travel farther into the tissue before exiting at the surface without being absorbed (photons that are absorbed cannot contribute to the photocurrent). Path length distributions and the penetration depth of photons that reach the sensor 122 vary as a function of emitter-sensor separation, with maximum effective photon depth penetration values several times greater than the physical emitter-sensor separation. For example, it has been determined that a spacing between the emitter 120 and the sensor 122 of 5 mm may permit detection of vessels from 0 mm to 12 mm from the surface of the tissue.

Changes in blood volume, due to differences in systolic and diastolic pressures within a tissue-embedded artery, affect the relative number of long-traveling photons that survive and reach the sensor 122. The temporally observed difference in the number of long-traveling photons that results from the presence of an artery in the photon trajectory is responsible for the pulsatile (AC) signal. For a small source-detector separation, detected photons traversing the shorter distances are less exposed to the cycling blood of an artery at a greater depth below the tissue surface, and therefore survive with a more uniform likelihood between systolic and diastolic conditions. With an increased source-detector separation, a higher percentage of photons that reach the sensor 122 will be long-traveling photons, resulting in larger detected pulse amplitudes. Therefore, it is believed that increasing the spacing between the emitter 120 and the sensor 122 may permit the light to penetrate even deeper into the tissue, permitting vessel detection at even greater depths.

It is further believed that adjusting the angle of the emitter 120 and/or sensor 122 may provide a similar effect. That is, similar to the way in which a change in the linear distance between the emitter 120 and the sensor 122 allows for the sampling of a different proportion of long-traveling photons at the surface sensor 122, a variation in angle of the emitter 120 and/or sensor 122 can change the depth and the distance to which the photons travel before being sampled by the sensor 122. Consequently, changes in the angle of the emitter and/or sensor are believed to permit the depth at which vessels can be detected by the instrument 106 to be varied.

Thus, according to the embodiments described herein, the emitter 120 and sensor 122 may be disposed to be mounted in a fixed relationship to each other, or a moveable or adjustable relationship. In particular, FIGS. 3 and 4 illustrate embodiments wherein emitter 120 and sensor 122 are at a fixed spacing relative to each other, and also have a fixed angular relationship between the emitter 120 and the sensor 122. Such an embodiment would permit the user to be confident that the vessels detected are within, for example, 12 mm from the working end 104 of the instrument 106. By contrast, the embodiment of FIG. 5 has the sensor 122 mounted in a first jaw 180 of the instrument 106 and the emitter 120 mounted in a second jaw 182 of the instrument 106. Such an embodiment would permit the user to vary the depth of detection simply by varying the distance between the jaws 180, 182 of the instrument 106: with the jaws 180, 182 closed, the user may probe for shallow vessels (i.e., vessels disposed within 12 mm of the tissue surface), while with the jaws 180, 182 open, the user may probe for deeper vessels (i.e., vessels disposed greater than 12 mm below the tissue surface). According to the embodiment illustrated in FIG. 5, the control structure for operating the jaws 180, 182 may include a mechanism for modifying the distance between the jaws 180, 182 in a controlled fashion (e.g., in discrete increments) so that the user can determine the jaw spacing (and thus the detection depth) without visualization of the jaws 180, 182.

As mentioned above, the light emitter 120 of any of FIGS. 3-5 may include one or more elements. According to such an embodiment, all of the elements may be adapted to emit light at a particular wavelength (e.g., 660 nm), or certain elements may emit light at different wavelengths than other elements. It is believed that a system with multiple light emitters 120 and/or multiple sensors 122 will increase the signal-to-noise ratio and the spatial resolution compared to a system containing a single emitter 120 and sensor 122.

As to those embodiments wherein the light emitter 120 is in the form of an array including one or more light emitting diodes, the diodes may be arranged in the form of a one-dimensional, two-dimensional or three-dimensional array. An example of a one-dimensional array may include disposing the diodes along a line in a single plane, while an example of a two-dimensional array may include disposing the diodes in a plurality of rows and columns in a single plane. Further example of a two-dimensional array may include disposing the diodes along a line on or in a curved surface. A three-dimensional array may include diodes disposed in more than one plane, such as in a plurality of rows and columns on or in a curved surface.

The light sensor 122 according to the embodiments of FIGS. 3-5 also may include one or more individual elements. As was the case with the light emitter 120, the elements of the light sensor 122 may be arranged in an array, and the discussion about the arrays above applied with equal force here.

In addition, the light sensor 122 may include a mechanism for physically excluding photons reaching the sensor 122 from a range of angles. This mechanism can consist of a mask or grated layer to physically filter any photons that are not reaching the sensor 122 at a nearly perpendicular angle. It has been observed that the mean depth penetration of the photons leaving the emitter 120 is equal to just over half the distance of source-detector separation (~2.5 mm penetration for our 5 mm spacing). This mechanism will increase the proportion of long-traveling and deep penetrating photons that are received by the sensor 122 thus increasing the depth at which the vessels can be detected by the instrument.

As to all of the foregoing embodiments, the system 100 may include hardware and software in addition to the emitter 120, sensor 122, and controller 124. For example, where more than one emitter 120 is used, a drive controller may be provided to control the switching of the individual emitter elements. In a similar fashion, a multiplexer may be provided where more than one sensor 122 is included, which multiplexer may be coupled to the sensors 122 and to an amplifier. Further, the controller 124 may include filters and analog-to-digital conversion as may be required.

According to certain embodiments, the splitter 126 and the analyzer 128 may be defined by one or more electrical circuit components. According to other embodiments, one or more processors (or simply, the processor) may be programmed to perform the actions of the splitter 126 and the analyzer 128. According to still further embodiments, the splitter 126 and the analyzer 128 may be defined in part by electrical circuit components and in part by a processor programmed to perform the actions of the splitter 126 and the analyzer 128.

For example, the splitter 126 may include or be defined by the processor programmed to separate the first pulsatile component from the second non-pulsatile component. Further, the analyzer 128 may include or be defined by the processor programmed to determine the presence of (or to quantify the size of, for example) the vessel V within the region 102 proximate to the working end 104 of the surgical instrument 106 based on the first pulsatile component. The instructions by which the processor is programmed may be stored on a memory associated with the processor, which memory may include one or more tangible non-transitory computer readable memories, having computer executable instructions stored thereon, which when executed by the processor, may cause the one or more processors to carry out one or more actions.

FIGS. 14 and 15 illustrate an embodiment of the surgical system 100 in combination with embodiments of a video system 200, such as may be used conventionally during minimally invasive surgery or laparoscopic surgery, for example. The video system 200 includes a video camera or other image capture device 202, a video or other associated processor 204, and a display 206 having a viewing screen 208.

As illustrated, the video camera 202 is directed at the region 102 proximate the working ends 104 of two surgical instruments 106. As illustrated, both of the surgical instruments 106 are part of an embodiment of a surgical system 100, such as illustrated in FIG. 2 and discussed above. In this case, the instruments 106 each include a visual indicator 130. It will be recognized, however, that according to other embodiments only one of the instruments 106 may include a visual indicator 130. The other elements of the surgical system 100 are omitted for ease of illustration, although it will be noted that elements of the system 100, such as the splitter 126 and the analyzer 128, may be housed in the same physical housing as the video processor 204.

The signal from the video camera 202 is passed to the display 206 via the video processor 204, so that the surgeon or other member of the surgical team may view the region 102 as well as the working ends 104 of the surgical instruments 106, which are typically inside the patient. Because of the proximity of the visual indicators 130 to the working ends 104, and thus the region 102, the visual indicators 130 are also visible on the display screen 108. As mentioned previously, this advantageously permits the surgeon to receive visual cues or alarms via the visual indicators 130 via the same display 206 and on the same display screen 208 as the region 102 and the working ends 104. This, in turn, limits the need of the surgeon to look elsewhere for the information conveyed via the visual indicators 130.

FIG. 15 illustrates another embodiment of a video system 200 that can be used in conjunction with an embodiment of the surgical system 100. According to this embodiment, the video processor 204 is not disposed in a housing separate from the video camera 202', but is disposed in the same housing as the video camera 202'. According to a further embodiment, the video processor 204 may be disposed instead in the same housing as the remainder of the display 206' as the display screen 208'. Otherwise, the discussion above relative to the embodiment of the video system 200 illustrated in FIG. 14 applies equally to the embodiment of the video system 200 illustrated in FIG. 15.

While the user interface 130 advantageously permits the surgeon or surgical team to view an output from the controller 124, it is possible to include other output devices with the user interface 130, as illustrated in FIGS. 1 and 2. For example, an alert may be displayed on a video monitor 300 being used for the surgery (e.g., the display 206, 206' in FIGS. 14 and 15), or may cause an image on the monitor to change color or to flash, change size or otherwise change appearance. The auxiliary output may also be in the form of or include a speaker 302 that provides an auditory alarm. The auxiliary output also may be in the form of or may incorporate a safety lockout associated with the surgical instrument 106 that interrupts use of the instrument 106. For example, the lockout could prevent ligation or cauterization where the surgical instrument 106 is a thermal ligature device. As a still further example, the auxiliary output also may be in the form of a haptic feedback system, such as a vibrator 304, which may be attached to or formed integral with a handle or handpiece of the surgical instrument 106 to provide a tactile indication or alarm. In addition to the light emitting elements disposed at the working end 104 of the surgical instrument 108, one or more light emitting elements may be disposed at the proximal end 110 of the shaft 108, such as disposed on or attached to the grip or handle 112, to provide a visual indication or alarm. Various combinations of these particular forms of the auxiliary output may also be used.

As mentioned above, the surgical system 100 may also include the surgical instrument 106 with the working end 104, to which the user interface 130 and the sensor (and in preferred embodiments, the light emitter 120 and the light sensor 122) are attached (in the alternative, removably/reversibly or permanently/irreversibly). The user interface 130 and sensor may instead be formed integrally (i.e., as one piece) with the surgical instrument 106. As also stated, it is possible that the user interface 130 and sensor be attached to a separate instrument or tool that is used in conjunction with a surgical instrument or tool 106.

As noted above, the surgical instrument 106 may be a thermal ligature device in one embodiment. In another embodiment, the surgical instrument 106 may simply be a grasper or grasping forceps having opposing jaws. According to still further embodiments, the surgical instrument may be other surgical instruments such as irrigators, surgical staplers, clip appliers, and robotic surgical systems, for example. According to still other embodiments, the surgical instrument may have no other function that to carry the user interface and sensor and to place them within a surgical field. The illustration of a single embodiment is not intended to preclude the use of the system 100 with other surgical instruments or tools 106.

In conclusion, although the preceding text sets forth a detailed description of different embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112(f).

What is claimed is:

1. A surgical system comprising:
a shaft having a distal end and a proximal end, the distal end having first and second jaws attached thereto and the proximal end including a grip,
a first plurality of line segments is disposed on one or both of the first and second jaws;
a sensor attached to the distal end of the shaft;
at least one visual indicator disposed spaced from the first and second jaws, a second plurality of line segments disposed over the at least one visual indicator, at least one of the line segments of the second plurality of line segments having a one-to-one correspondence to at least one of the line segments of the first plurality of line segments; and
a controller coupled to the sensor and the at least one visual indicator, the controller configured to actuate a portion of the at least one visual indicator according to a signal received from the sensor, the portion of the at least one visual indicator representing a location of a vessel between the first and second jaws attached to the distal end of the shaft.

2. The surgical system according to claim 1, the sensor attached to the distal end of the shaft by being disposed on at least one of the first and second jaws.

3. The surgical system according to claim 2, wherein the sensor comprises a light sensor and a light emitter, the light emitter disposed on at least one of the first and second jaws.

4. The surgical system according to claim 3, wherein the light emitter is attached to the first jaw and the light sensor is attached to the second jaw.

5. The surgical system according to claim 1, wherein the at least one visual indicator is integral with the shaft.

6. The surgical system according to claim 5, wherein the at least one visual indicator is integral with a portion of the distal end of the shaft spaced from the first and second jaws.

7. The surgical system according to claim 1, wherein the at least one visual indicator comprises at least one light emitting element.

8. The surgical system according to claim 7, wherein the at least one visual indicator comprises an array of light emitting elements.

9. The surgical system according to claim 8, wherein individual elements of the array are continuous.

10. The surgical system according to claim 8, wherein individual elements of the array are not contiguous.

11. The surgical system according to claim 10, further comprising spacers disposed between the individual elements of the array.

12. The surgical system according to claim 8, wherein individual elements of the array provide light of different colors.

13. The surgical system according to claim 8, wherein the portion of the at least one visual indicator comprises at least one of the light emitting elements of the array of light emitting elements.

14. The surgical system according to claim 1, wherein the grip is defined along a length of the shaft.

15. The surgical system according to claim 1, wherein the first and second jaws each have a length, and the line segments of the first plurality of line segments are transverse to the length of a respective one of the one or both of the first and second jaws.

16. The surgical system according to claim 15, wherein the line segments are of varying transverse length.

17. The surgical system according to claim 16, wherein the line segments are in a repeating pattern of varying transverse lengths.

18. The surgical system according to claim 15, wherein alphanumeric indicia is associated with the line segments.

19. The surgical system according to claim 1, wherein:

the first and second jaws each have a length, and the line segments of the first plurality of line segments are transverse to the length of a respective one of the one or both of the first and second jaws, the at least one visual indicator has a length, and the line segments of the second plurality of line segments are transverse to the length of the at least one visual indicator, and the line segments of the second plurality of line segments have a one-to-one correspondence to the line segments of the first plurality of line segments.

20. The surgical system according to claim 19, wherein:

the line segments of the first plurality of line segments and the second plurality of line segments are both in a repeating pattern of varying transverse lengths, and alphanumeric indicia is associated with the line segments.

* * * * *